United States Patent [19]

Abichandani et al.

[11] Patent Number: 5,625,103

[45] Date of Patent: Apr. 29, 1997

[54] CONTINUOUS TOLUENE DISPROPORTIONATION PROCESS

[75] Inventors: Jeevan S. Abichandani, Voorhees; Jeffrey S. Beck, Princeton; Ronald H. Fischer, Cherry Hill; Ivy D. Johnson, Medford; David L. Stern, Lawrenceville, all of N.J.

[73] Assignee: Mobil Oil Corporation, Fairfax, Va.

[21] Appl. No.: 441,105

[22] Filed: May 15, 1995

[51] Int. Cl.$^6$ .................................................. C07C 5/52
[52] U.S. Cl. ............................................ 585/475; 585/474
[58] Field of Search ................................. 585/475, 474, 585/466

[56] References Cited

U.S. PATENT DOCUMENTS

| | | | |
|---|---|---|---|
| 3,698,157 | 10/1972 | Allen et al. | 260/674 SA |
| 3,780,122 | 12/1973 | Pollizter | 585/474 |
| 4,060,568 | 11/1977 | Rodewald | 260/682 |
| 4,090,981 | 5/1978 | Rodewald | 252/455 Z |
| 4,100,215 | 7/1978 | Chen | 260/671 M |
| 4,127,616 | 11/1978 | Rodewald | 260/671 R |
| 4,145,315 | 3/1979 | Rodewald | 252/455 Z |
| 4,379,761 | 4/1983 | Olson et al. | 585/466 |
| 4,465,886 | 8/1984 | Rodewald | 585/467 |
| 4,477,583 | 10/1984 | Rodewald | 502/71 |
| 4,665,258 | 5/1987 | Butler et al. | 585/475 |
| 4,927,979 | 5/1990 | Yamagishi et al. | 568/791 |
| 4,950,835 | 8/1990 | Lee et al. | 585/467 |
| 5,173,461 | 12/1992 | Absil et al. | 502/62 |
| 5,243,117 | 9/1993 | Chang et al. | 585/475 |
| 5,367,099 | 11/1994 | Beck et al. | 585/475 |
| 5,387,732 | 2/1995 | Shamshoum et al. | 585/475 |
| 5,475,180 | 12/1995 | Shamshoum et al. | 585/475 |

*Primary Examiner*—Glenn A. Caldarola
*Attorney, Agent, or Firm*—P. W. Roberts; M. D. Keen

[57] ABSTRACT

There is provided a continuous toluene disproportionation process to selectively produce para-xylene. The process includes a steady-state of operation, wherein the conversion of toluene and selectivity to para-xylene is maintained at essentially constant target levels. Prior to such a steady-state of operation, the reaction is conducted under a relatively high temperature.

11 Claims, 8 Drawing Sheets

FIG. 1  NART VS. DAYS ON STREAM

CONTINUOUS TOLUENE DISPROPORTIONATION PROCESS

BACKGROUND

There is provided a continuous toluene disproportionation process.

Shape-selective catalysis is described, e.g., by N. Y. Chen, W. E. Garwood, and F. G. Dwyer, *Shape Selective Catalysis in Industrial Applications*, 36, Marcel Dekker, Inc. (1989). Within a zeolite pore, hydrocarbon conversion reactions such as isomerization, disproportionation, alkylation, and transalkylation of aromatics are governed by constraints imposed by the channel size. Reactant selectivity may occur when a fraction of the feedstock is too large to enter the zeolite pores to react, while product selectivity may occur when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape-selective catalysis is demonstrated, for example, in selective alkyl-substituted benzene disproportionation to para-dialkyl-substituted benzene.

A representative para-dialkyl-substituted benzene is para-xylene. The production of para-xylene may be performed by methylation of toluene or by toluene disproportionation over a catalyst under conversion conditions. Examples include the reaction of toluene with methanol, as described by Chen et al., *J. Amer. Chem. Soc.*, 101, 6783 (1979), and toluene disproportionation, as described by Pines in *The Chemistry of Catalytic Hydrocarbon Conversions*, Academic Press, 72 (1981). Such methods may result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

U.S. Pat. No. 4,283,306 to Herkes discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation.

Noble metals, such as platinum, have been incorporated into catalysts for toluene disproportionation reactions for the purpose of reducing the generation of the unwanted by-product, ethylbenzene.

SUMMARY

There is provided a process for disproportionating toluene, said process comprising contacting toluene with a catalyst under conditions sufficient to disproportionate toluene, said catalyst comprising ZSM-5, said catalyst being selectivated with a siliceous material, wherein said process comprises an adjustment phase and at least one steady-state phase, wherein said adjustment phase comprises introducing toluene into a reactor comprising said catalyst under conditions sufficient to increase the para-selectivity of said catalyst, wherein said steady-state phase comprises introducing toluene into said reactor under conditions sufficient to achieve essentially constant levels of toluene conversion and para-xylene selectivity, the inlet temperature of said reactor being incrementally adjusted upwardly to compensate for aging of said catalyst, wherein, prior to a steady state phase, the inlet temperature of said reactor is maintained continuously for a period of at least 9 hours at a temperature which is at least 20° C. greater than the average inlet temperature of said reactor during the first 10 days of operation of said steady-state phase.

EMBODIMENTS

In a process for the selective production of para-xylene by the disproportionation of toluene over a selectivated catalyst, it is desirable to operate the process in a steady-state fashion, wherein essentially constant levels of toluene conversion and para-selectivity are maintained. In this regard, it will be understood that para-selectivity refers to the percentage of para-xylene in the overall mixture of xylene isomers obtained. For example, during such a steady-state phase of operation, the conversion of toluene may vary by only a small amount, e.g., ±about 2 wt. %, from a target conversion rate, e.g., selected from a particular percentage in the range of from about 25% to about 35%, such as about 30%. Similarly, the para-selectivity may vary by only a small amount, e.g., ±about 2%, from a target para-selectivity, e.g., selected from a particular percentage in the range of from about 85% to about 95%, such as about 91%.

In order to compensate for reduced activity of the catalyst, brought about primarily by coking, the conditions of the reaction must be adjusted periodically to maintain the steady-state of operation. This adjustment is generally made by incrementally increasing the temperature of the reaction. For example, the temperature of the reaction may be increased on a daily basis in an amount sufficient to return the reaction to the target level of conversion. In such a case the average daily rate of temperature increase in the reactor provides a measure of the aging rate of the catalyst. Depending upon the aging rate of the catalyst, the steady-state of operation may be maintained for an extended period, e.g., for at least 30 days or even at least 100 days. When the catalyst becomes sufficiently aged such that steady-state operation is no longer practical, the reaction may be interrupted and the catalyst regenerated.

When fresh catalyst is first loaded into the reactor, it may not be possible or practical to maintain a steady-state of operation during the initial stages of the reaction. More particularly, it has been observed that the para-selectivity of toluene disproportionation may increase during the initial stages of a reaction, especially when the catalyst comprises ZSM-5 selectivated with a siliceous material. While not wishing to be bound by any theory, it is theorized that a small amount of coke must be deposited on certain catalysts before the targeted level of para-selectivity is achieved. This initial phase of operation, prior to steady-state operation, is also referred to herein as the adjustment phase or the line-out period. The para-selectivity of the reaction may increase by at least 5%, e.g., from less than 85% to greater than 90%, during the adjustment phase.

It has now been discovered that benefits are derived from operating the reaction at a relatively high temperature and then dropping the temperature down to start a steady-state of operation. When a high temperature is employed in the adjustment phase, the duration of this phase (i.e., the time it takes to reach the target para-selectivity) is reduced. Furthermore, high temperature operation has been observed to improve the stability (i.e., reduce the aging rate) of the catalyst during a subsequent steady-state operation. This improved stability is observed whether the high temperature is employed during the initial adjustment phase or at some point intermediate to successive steady-states of operation. For example, the reaction may be run under an initial adjustment phase to achieve the target level of para-selectivity, followed by a first steady-state phase, followed by a brief period where the temperature of the reactor is raised, followed by a second steady-state phase, wherein the temperature is lowered to achieve the level of conversion obtained in the first steady-state phase. The aging rate of the catalyst during the second steady-state phase will be lower than the aging rate of the catalyst during the first steady state of operation. The period of high temperature operation may be at at least 9 hours, e.g., at least 18 hours, e.g., least 24 hours, e.g., from about one day to about five days. The inlet temperature of the reactor may be at least 20° C. higher during the period of high temperature operation, Ks compared with the average inlet temperature of the same reactor during the first 10 days, or even the first 100 days, of the subsequent steady-state operation.

ZSM-5 may be selectivated with a siliceous material by a vapor phase process or a liquid phase process. An example of a liquid phase selectivation process is described herein as a preselectivation or ex situ selectivation process. The preselectivation treatment involves depositing siliceous material on the catalyst by the steps of:

(a) combining ZSM-5 with an organosilicon compound; and (b) calcining the organosilicon containing material in an oxygen containing atmosphere under conditions sufficient to remove organic material therefrom and leave the siliceous material on the ZSM-5.

Examples of preselectivation techniques are provided in copending U.S. patent application Ser. Nos. 08/069,251; 069,254; 08/069,255; and 08/069,259, each filed May 28, 1993. Ser. No. 08/069,254 is now U.S. Pat. No. 5,367,099; Ser. No. 08/069,255 is now U.S. Pat. No. 5,404,800; and Ser. No. 08/069,259 is now U.S. Pat. No. 5,365,004.

The preselectivation treatment may result in the deposition of at least 1 wt % of siliceous material on the catalyst.

ZSM-5 may be combined with a binder material for the ZSM-5. This binder material is preferably an inert, non-alumina binder material, such as a silica binder. ZSM-5 may be subjected to one or more selectivation treatments after the ZSM-5 is combined with the binder material. Optionally, however, the ZSM-5 may be selectivated in the unbound state.

Procedures for preparing silica bound zeolites, such as ZSM-5, are described in U.S. Pat. Nos. 4,582,815; 5,053,374; and 5,182,242. A particular procedure for binding ZSM-5 with a silica binder involves an extrusion process.

A particular process for preparing silica bound ZSM-5 may comprise the steps of:

(a) mulling and then extruding a mixture comprising water, ZSM-5, colloidal silica and sodium ions under conditions sufficient to form an extrudate having an intermediate green strength sufficient to resist attrition during ion exchange step (b) set forth hereinafter;

(b) contacting the uncalcined extrudate of step (a) with an aqueous solution comprising ammonium cations under conditions sufficient to exchange cations in said ZSM-5 with ammonium cations; and (c) calcining the ammonium exchanged extrudate of step (b) under conditions sufficient to generate the hydrogen form of said ZSM-5 and increase the crush strength of said extrudate.

In accordance with examples of a preselectivation technique, the catalyst may be preselectivated by single or multiple treatments with a liquid organosilicon compound in a liquid carrier, each treatment being followed by calcination of the treated material in an oxygen containing atmosphere, e.g., air.

In accordance with the multiple impregnation preselectivation method, the ZSM-5 is treated at least twice, e.g., at least 3 times, e.g., from 4 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant.

Stable aqueous emulsions of organosilicon compounds (e.g., silicone oil) are described in copending U.S. patent application Ser. No. 08/141,758, filed Oct. 27, 1993. These emulsions are generated by mixing the organosilicon oil and an aqueous component in the presence of a surfactant or surfactant mixture. Useful surfactants include any of a large variety of surfactants, including ionic and non-ionic surfactants. Preferred surfactants include non-nitrogenous non-ionic surfactants such as alcohol, alkylphenol, and polyalkoxyalkanol derivatives, glycerol esters, polyoxyethylene esters, anhydrosorbitol esters, ethoxylated anhydrosorbitol esters, natural fats, oils, waxes and ethoxylated esters thereof, glycol esters, polyalkylene oxide block co-polymer surfactants, poly(oxyethylene-co-oxypropylene) non-ionic surfactants, and mixtures thereof. More preferred surfactants include surfactants having the formula α-[4-(1,1,3,3-tetramethylbutyl)phenyl]-ω-hydroxypoly(oxy-1,2-ethanediyl) (Octoxynols), most preferably octoxynol-9. Such preferred surfactants include the TRITON® X series, such as TRITON®X-100 and TRITON®X-305, available from Rohm & Haas Co., Philadelphia, Pa., and the Igepal Calif. series from GAF Corp., New York, N.Y. Emulsions formulated using such surfactants are effective for selectivating ZSM-5 to enhance shape selectivity, and to passivate surface acidity detrimental to product selectivity in certain regioselective catalytic applications such as the disproportionation of alkylbenzenes.

The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl—silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenylmethyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as —N(CH$_3$)$_3$, —N(C$_2$H$_5$)$_3$ and —N(C$_3$H$_7$)$_3$. A preferred water soluble organosilicon preselectivating agent is an n-propylamine silane, available as Hydrosil 2627 from Huls America.

When the ZSM-5 is preselectivated by a single or multiple impregnation technique, the ZSM-5 is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This calcination temperature may be below 700° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., N$_2$, atmosphere. An example of an oxidizing atmosphere is an oxygen containing atmosphere, such as air. Calcination may take place initially in an inert, e.g., N$_2$, atmosphere, followed by calcination in an oxygen containing atmosphere, such as air or a mixture of air and N$_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

Preferably, the kinetic diameter of both the organosilicon compound, which is used to preselectivate the zeolite, and the organosilicon compound (e.g., silicone compound), which is used to functionalize the zeolite, is larger than the zeolite pore diameter, in order to avoid entry of the organosilicon compound into the zeolite pores and any concomitant reduction in the internal activity of the zeolite.

The selectivated ZSM-5 is a catalyst. This catalyst may be used alone or in combination with other catalyst components included in catalysts of this type. Such other components include binders and hydrogenation/dehydrogenation components. Accordingly, it will be understood that the term, present catalyst, as used herein is intended to connote the presently selectivated zeolite in combination with other catalyst components, if any.

The present zeolite may optionally be treated, before, during or after contact with the organosilicone selectivating agent, with selectivating agents containing atoms other than silicon or carbon. Such optional selectivation agents may include atoms such as P, Mg, B, N, Ce, Ca and Sr. However, insofar as the present catalyst may be free of treatment with such optional selectivation agents, the present catalyst may contain less than 500 ppm of each of the following elements as measured by elemental analysis: P, Mg, B, N, Ce, Ca, and Sr.

While not wishing to be bound by any theory, it is theorized that the extreme selectivity of the present catalyst is obtained by rendering acid sites on the external surfaces of the zeolite substantially inaccessible to reactants, while possibly increasing the tortuosity of the catalyst pore system. In a toluene disproportionation process using a non-selectivated catalyst, acid sites existing on the external surfaces of the zeolite are believed to isomerize the product para-xylene back to an equilibrium level with the other two xylene isomers, thereby reducing the amount of para-xylene in the xylenes to only about 24%. By reducing the availability of these external acid sites to the product para-xylene, it is theorized that a relatively high proportion of the para isomer can be retained. It is theorized that external zeolite acid sites are blocked or otherwise unavailable to para-xylene in the present catalyst. The extreme para-selectivity of the present catalyst is especially surprising in the highly active forms of the catalyst.

The "alpha value" of a catalyst is an approximate indication of its catalytic cracking activity. The alpha test is described in U.S. Pat. No. 3,354,078 and in the *Journal of Catalysis*, Vol. 4, 522–529 (1965); Vol. 6, 278 (1966); and Vol. 61, 395 (1980), each incorporated herein by reference to that description. It is noted that intrinsic rate constants for many acid-catalyzed reactions are proportional to the alpha value for a particular crystalline silicate catalyst (see "The Active Site of Acidic Aluminosilicate Catalysts," *Nature*, vol. 309, No 5959, 589–591, (1984)). The experimental conditions of the alpha test preferably include a constant temperature of 538° C. and a variable flow rate as described in detail in the *Journal of Catalysis*, Vol. 61, 395 (1980). The present catalysts may have an alpha value greater than 50, e.g., greater than 200, e.g., from about 200 to about 1500. The alpha value of the catalyst may be increased by mild steaming before selectivation. This type of steaming is discussed in U.S. Pat. No. 4,326,994.

The silica to alumina ratio of zeolites may be determined by conventional analysis. This ratio is meant to represent, as closely as possible, the ratio in the rigid atomic framework of the zeolite crystal and to exclude silicon or aluminum in the binder or in cationic or other form within the channels. The silica to alumina molar ratio of the ZSM-5 used to prepare the present catalysts may be less than 60, e.g., less than 40, e.g., from about 20 to about 40. It will be appreciated that it may be extremely difficult to directly measure the silica to alumina ratio of zeolite after it has been combined with a binder material and selectivated by methods described hereinabove. Accordingly, the silica to alumina ratio has been expressed hereinabove in term of the silica to alumina ratio of the parent zeolite, i.e., the zeolite used to prepare the catalyst, as measured prior to the selectivation of the zeolite and prior to the combination of this zeolite with the other catalyst components.

The crystal size of the parent zeolites of the present catalysts is preferably greater than 0.1 microns, as calculated by methods described hereinbelow. The accurate direct measurement of the crystal size of zeolite materials is frequently very difficult. Microscopy methods, such as SEM and TEM, may be used, but these methods require measurements of a large number of crystals and, for each crystal measured, values may be evaluated in up to three dimensions. Furthermore, in order to more completely characterize the crystal size of a batch of crystals, one should calculate the average crystal size, as well as the degree of variance from this average in terms of a crystal size distribution. Rather than relying upon such complex evaluations, crystal size is expressed herein in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion*, Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d = 0.0704 \times t_{0.3}^{1/2}$$

Particular measurements expressed herein were made on a computer controlled, thermogravimetric electrobalance, but there are numerous ways one skilled in the art could obtain the data. Examples of larger crystal material have a sorption time, $t_{0.3}$, of 497 minutes, which gives a calculated crystal size of 1.6 microns. Examples of smaller crystal material have a sorption time of 7.8 minutes, and a calculated size of 0.20 microns.

As pointed out in the aforementioned U.S. Pat. No. 4,117,026, larger crystal size zeolites tend to have a greater intrinsic para-selectivity than smaller crystal size zeolites. It is theorized that this difference is attributable to the smaller ratio of external surface area to available internal surface area for larger zeolites as compared to smaller crystal size zeolites. Since it would theoretically require less selectivation to neutralize the external surface area of the more intrinsically para-selective larger crystal size zeolites, larger crystal size zeolites would be preferred to smaller crystal size zeolites, provided that all other factors were equal. However, there are other factors which tend to mitigate against a preference for larger crystal size zeolites, particularly ZSM-5. More particularly, larger crystal size ZSM-5 having a high activity and corresponding low silica to alumina molar ratio, e.g., from about 20 to about 40, is considerably more difficult to prepare than smaller crystal size ZSM-5, especially on a commercial scale. A particularly surprising aspect of the present siliceous material selectivated catalysts is that the zeolites thereof may comprise relatively small crystal size ZSM-5, e.g., having a crystal size of from about 0.1 to about 0.5 microns and a silica to alumina molar ratio of from about 20 to 40, and still have an extremely high degree of para-selectivity. When larger crystal size ZSM-5 is chosen for the present catalyst, this the crystal size of this ZSM-5 may be, for example, from about 1 to 2 microns.

The present catalyst is particularly adapted for the production of para-xylene via the catalytic disproportionation of toluene. More particularly, this catalyst, under disproportionation conditions, is capable of high conversions of toluene, while at the same time producing a very high proportion of para-xylene among the total of the xylene isomers. However, it will be understood that this catalyst may also be used to catalyze other organic, especially hydrocarbon, conversion reactions.

When the present catalyst is used in a toluene disproportionation reaction, the reaction conditions may include a temperature of about 350° C.–540° C., a pressure of about atmospheric—5000 psig, a toluene feed rate of about 0.1–20 WHSV, and a hydrogen to toluene mole ratio of about 0.1–20. The hydrogen cofeed serves to suppress catalyst aging, thereby dramatically increasing the cycle length.

The liquid feedstock for the present toluene disproportionation reaction may, optionally, include hydrocarbons other than toluene. Such hydrocarbons include non-aromatic hydrocarbons, such as paraffins and/or cycloparaffins. These non-aromatics may have boiling points close to the boiling point of toluene, which is about 111° C. These non-aromatics are, therefore, difficult to remove from toluene by distillation, and extraction techniques may be needed to separate these toluene coboilers from toluene. The amount of non-aromatics in the fresh feed may be from 0 wt. % to about 3 wt. %, e.g., from about 0.2 wt. % to about 1.5 wt. %. It will also be understood that commercial toluene disproportionation reactions are run by recycling unconverted toluene. The amount of recycled toluene in the feed to the reactor will vary on the amount of toluene conversion per pass. For example, this feed may comprise from about 50 wt. % to about 85 wt. % of recycled toluene. As a result, difficult to remove non-aromatic constituents (e.g., toluene coboilers) may build up in the recycle stream. These toluene coboilers may eventually comprise from about 2 wt. % to about 15 wt. % of the toluene recycle stream. Thus, the total liquid feed to the present disproportionation reactor may comprise both fresh (i.e., make-up) toluene and recycled toluene, and this liquid feed may comprise from 0 wt. % to about 15 wt. % of non-aromatics.

The present catalyst may, optionally, include a binder material.

The optional binder for the present catalyst is preferably an inert, non-alumina containing material, such as silica. However, the binder may also be selected from other materials which may be used exclusively or in combination with one another or with silica. Examples of such binder materials include alumina, zirconia, magnesia, titania, thoria and boria. These materials may be used in the form of dried inorganic oxide gels of gelatinous precipitates. Examples of clay binder materials include bentonite and kieselguhr. The relative proportion of zeolite to the binder material may be about 30 to about 90 percent by weight. The bound catalyst may be in the form of an extrudate, beads or fluidizable microspheres.

Optionally, the present catalyst may contain a hydrogenation/dehydrogenation component. Examples of such optional components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are particular optional hydrogenation/dehydrogenation components. Combinations of catalytic forms of such noble or non-noble metal, such as combinations of Pt with Sn, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction. Preferably, the present catalyst is free of noble metal.

The optional hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetrammineplatinum complexes, platinum chloride, tin sulfate and tin chloride.

The amount of optional hydrogenation/dehydrogenation component may be that amount which imparts or increases the catalytic ability of the overall catalyst to catalytically hydrogenate or dehydrogenate an organic compound under sufficient hydrogenation or dehydrogenation conditions. This amount is referred to herein as a catalytic amount. Quantitatively speaking, when the present catalyst comprises a noble metal, it may comprise, for example, from about 0.001 to about 5 wt %, e.g., from about 0.1 to about 2 wt %, of the noble metal.

EXAMPLE 1

Figure 1:
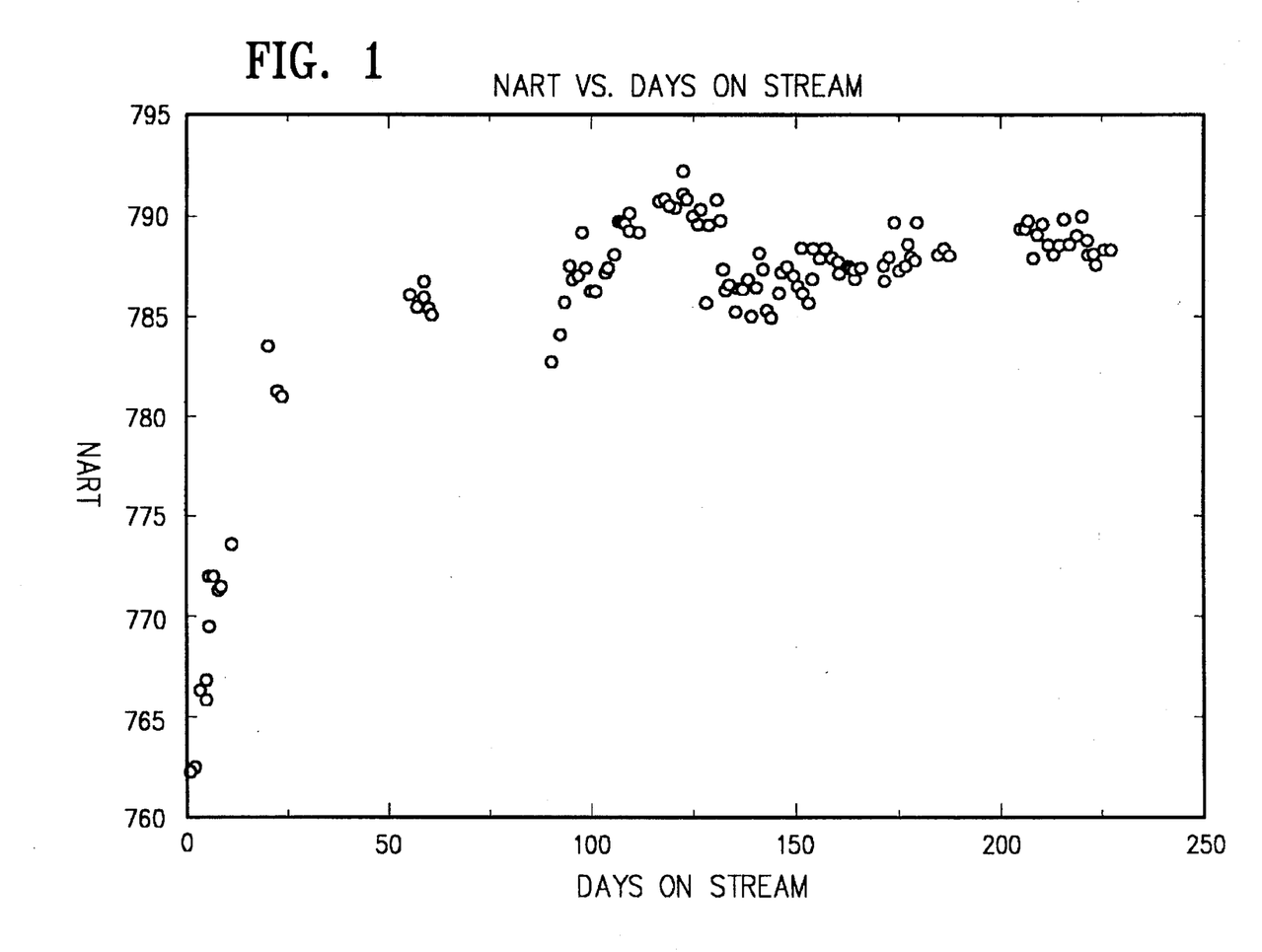
FIG. 1 is a graph showing the normalized average reactor temperature (NART) for a toluene disproportionation reaction versus the days on stream for the reactor.
Figure 2:
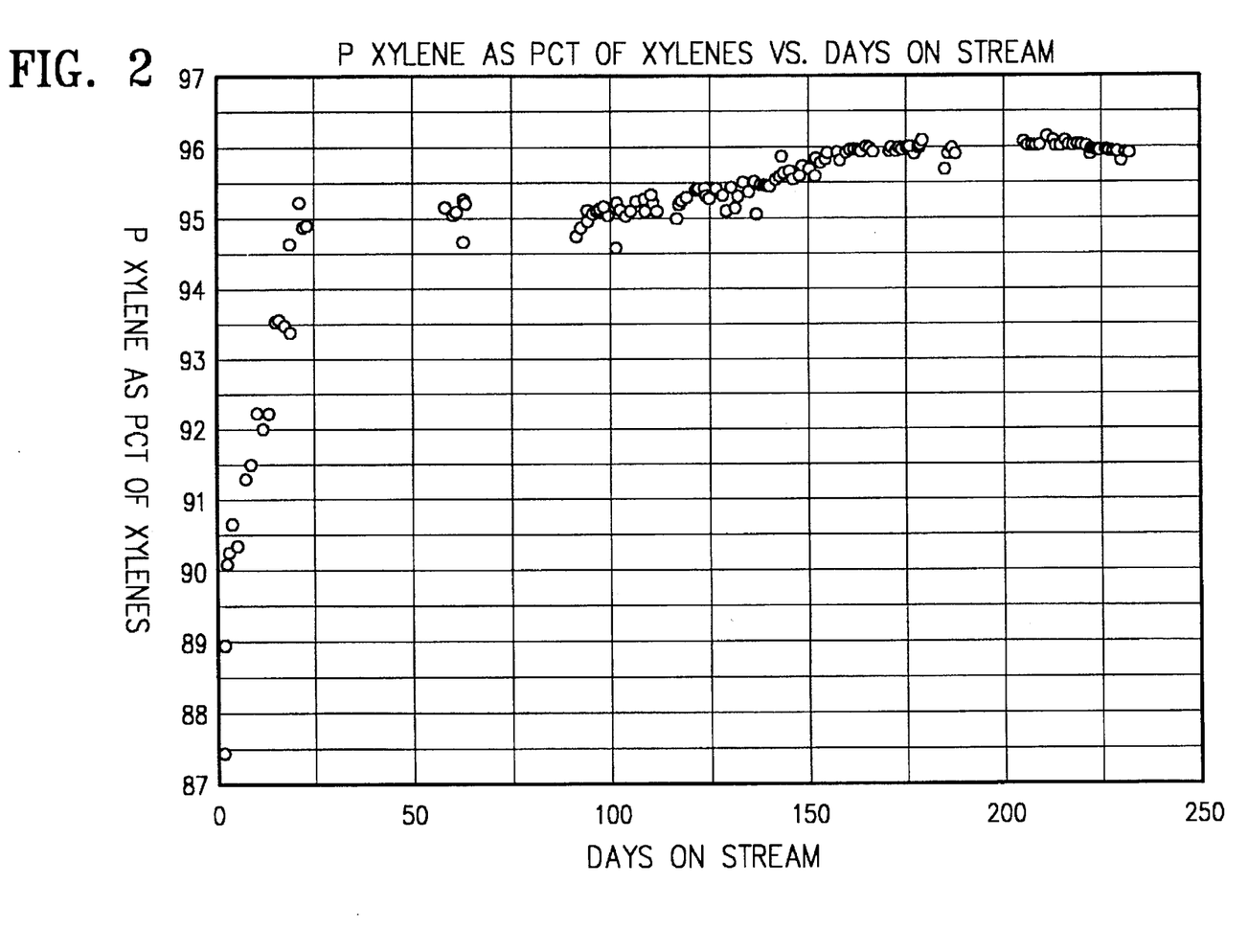
FIG. 2 is a graph showing para-selectivity, in terms of para-xylene as a percentage of total xylenes, versus days on stream for a toluene disproportionation reaction.
Figure 3:
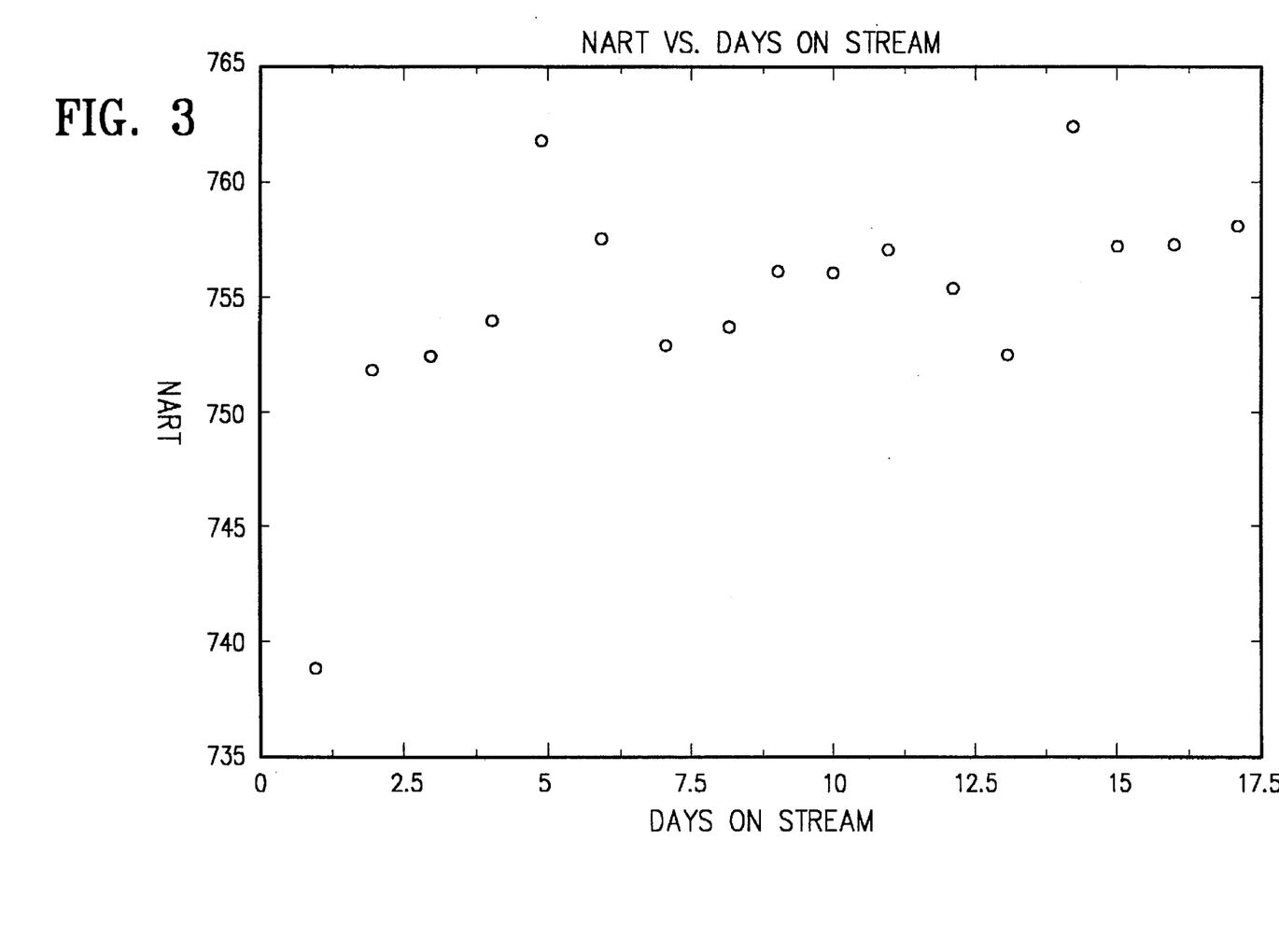
FIG. 3 is a graph showing the normalized average reactor temperature (NART) for a toluene disproportionation reaction versus the days on stream for the reactor.
Figure 4:
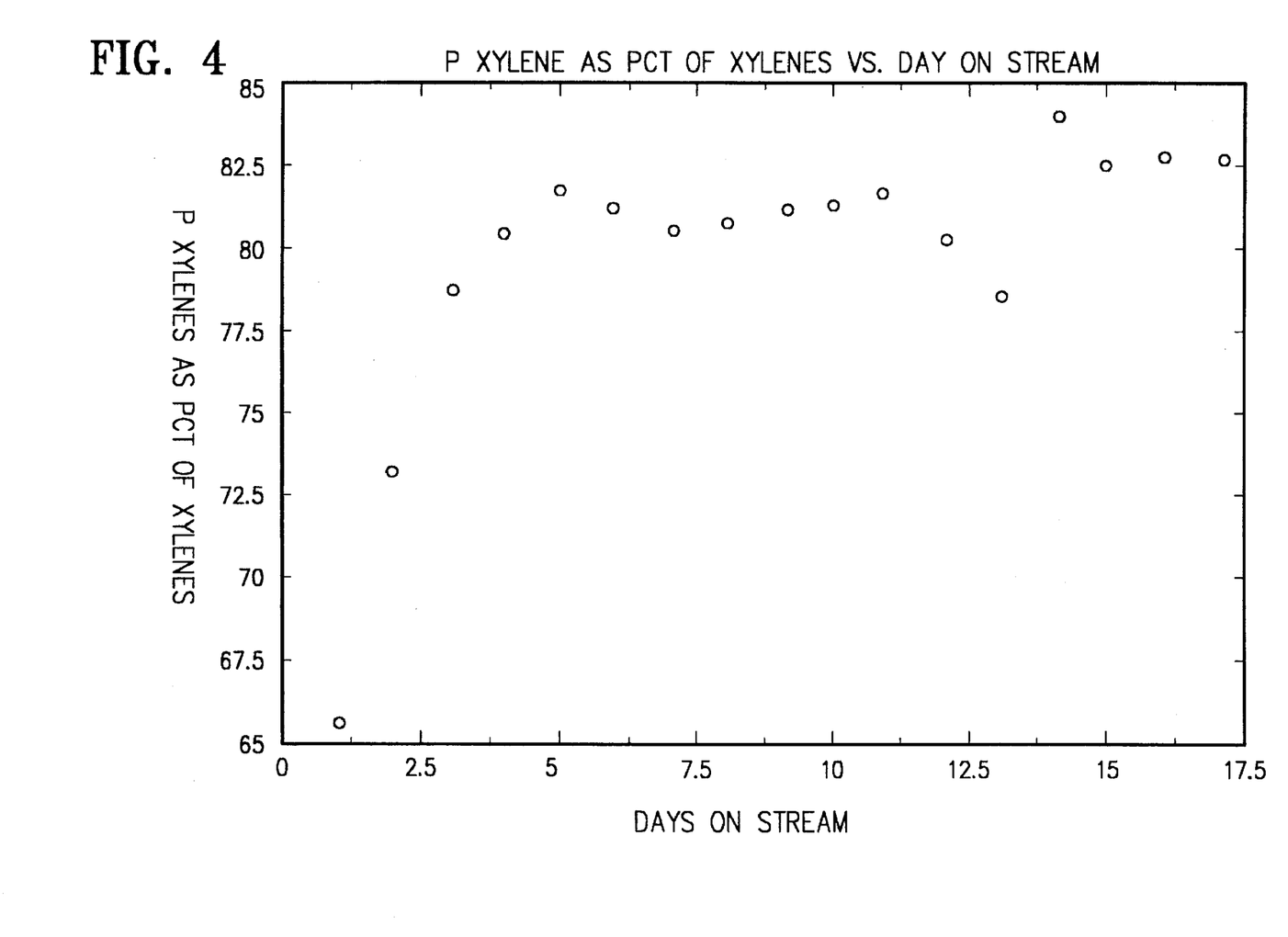
FIG. 4 is a graph showing para-selectivity, in terms of para-xylene as a percentage of total xylenes, versus days on stream for a toluene disproportionation reaction.

FIG. 1 shows a graph of Normalized Average Reactor Temperature (NART) versus Days on Stream. The reactor temperature is normalized to 30% conversion by carrying out an experiment which determines the relationship between conversion of toluene and temperature. For the reaction shown in FIG. 1, this relationship is 6.5° F. per 1% of toluene conversion. FIG. 1 indicates that it requires virtually 20 days to achieve the steady-state condition of relatively constant NART. This is also exhibited in FIG. 2 which shows the selectivity to p-xylene, the valuable product sought in this reaction. During the 20 day adjustment period prior to steady-state operation, significantly lower amounts of the highly valuable product of p-xylene is produced than during the steady-state. FIG. 3 shows a similar process, but in this case, the operation was initiated at much higher temperature than the steady-state temperature. Here the Normalized Average Reactor Temperature (NART) was at 780° F. versus 750° F. for the steady-state. In this case the selectivity was high from the beginning of the operation, thereby avoiding formation of lower valued products. This is shown in FIG. 4 where it is observed that p-xylene selectivity attains its steady-state level after the third day on stream.

Further data are shown in Table 1. Operations 1 and 2 in Table 1 shows the same catalyst as in FIG. 2. In Operation 1 the catalyst was brought on stream at 752° for 15 hours. After 32 hours at 740° F., it shows 73% p-xylene selectivity at 30% toluene conversion. The same catalyst was brought on stream at much higher initial temperature (Operation 2) of 842° F. for 16 hours; then the temperature was lowered to 754° F. to achieve 30% toluene conversion. After a total of 32 hours on stream at 30% toluene conversion, the selectivity of the catalyst was 81% p-xylene.

TABLE 1

| Operation | 1<br>No initial<br>Coking | 2<br>Initial<br>Coking |
|---|---|---|
| Time on Stream, Hrs. | 32 | 32 |
| Toluene Conversion, Wt. % | 30 | 30 |
| P-Xylene Selectivity | 75 | 81 |
| Selectivation Temperature, °F. | 752 (15 Hrs) | 842 (16 Hrs) |

In Examples 2–8, which follow, the toluene disproportionation reaction is monitored and the inlet temperature adjusted such that the toluene conversion is 30%. To monitor the progress of the catalyst and to normalize for daily fluctuations in the conversion, a normalized temperature for 30% toluene conversion (NART: Normalized Average Reactor Temperature) is plotted versus days on stream (DOS).

Figure 5:
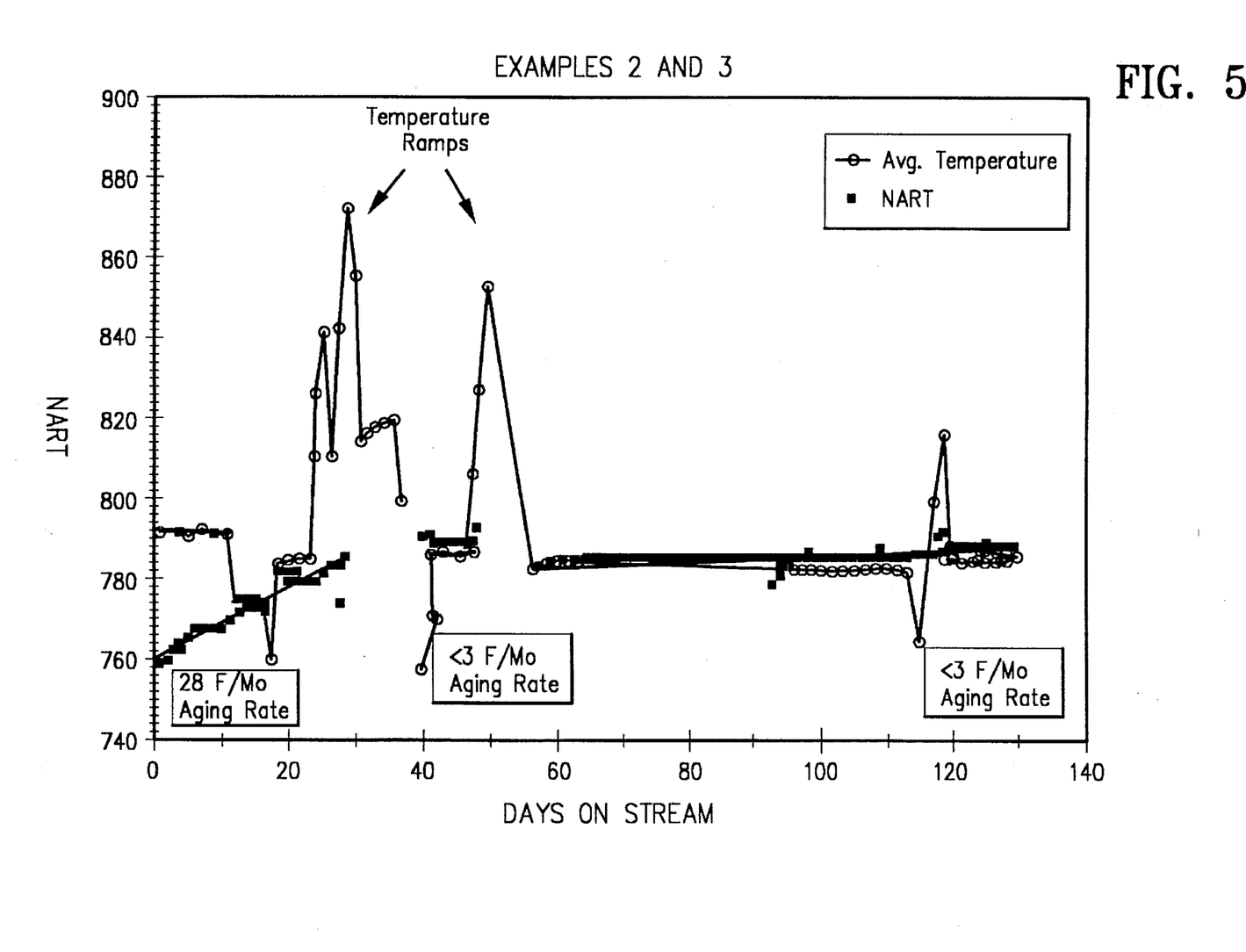
FIGS. 5, 6, and 7 are graphs showing reactor temperatures for a toluene disproportionation reaction versus the days on stream for the reactor.
Figure 6:
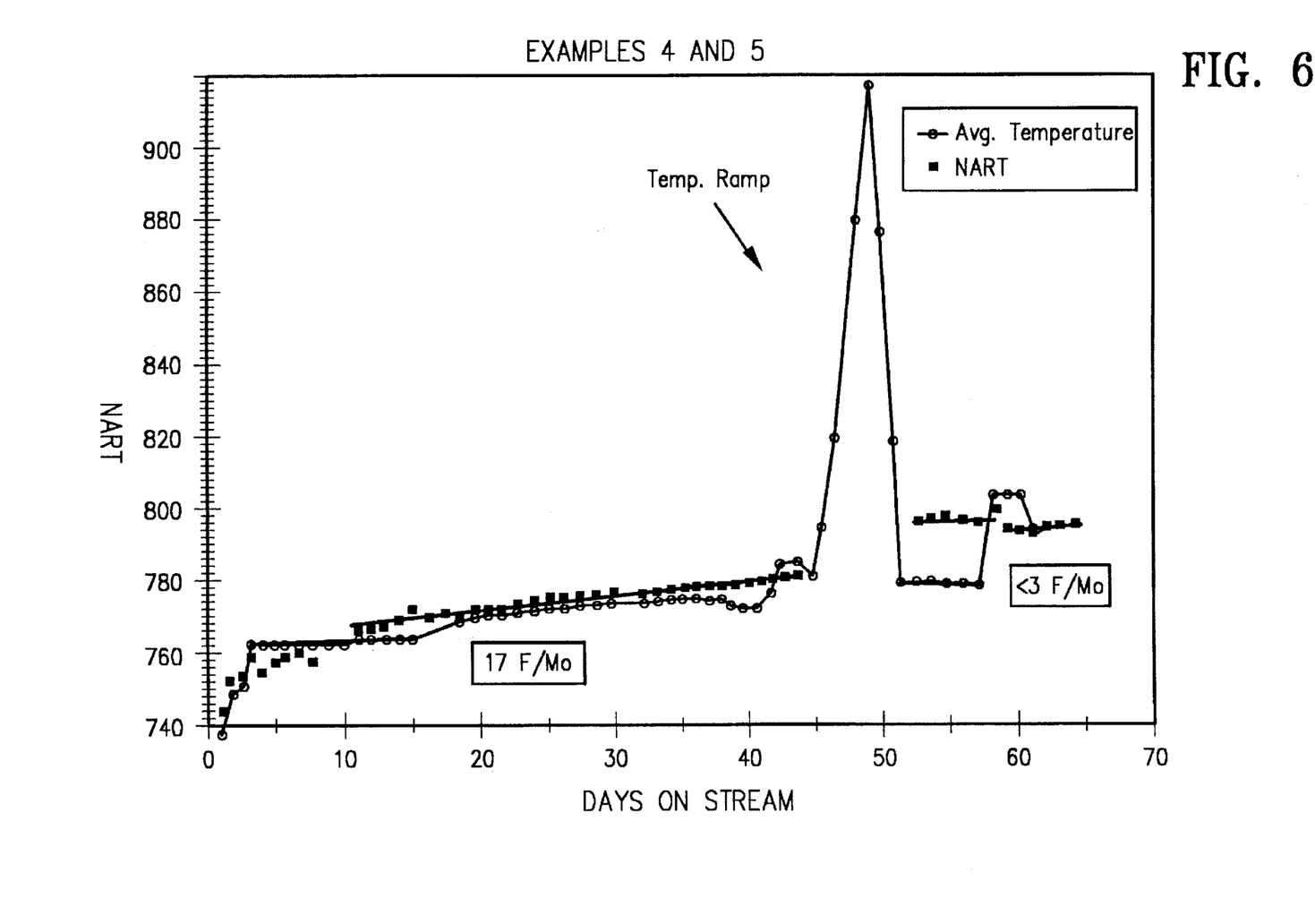
Figure 7:
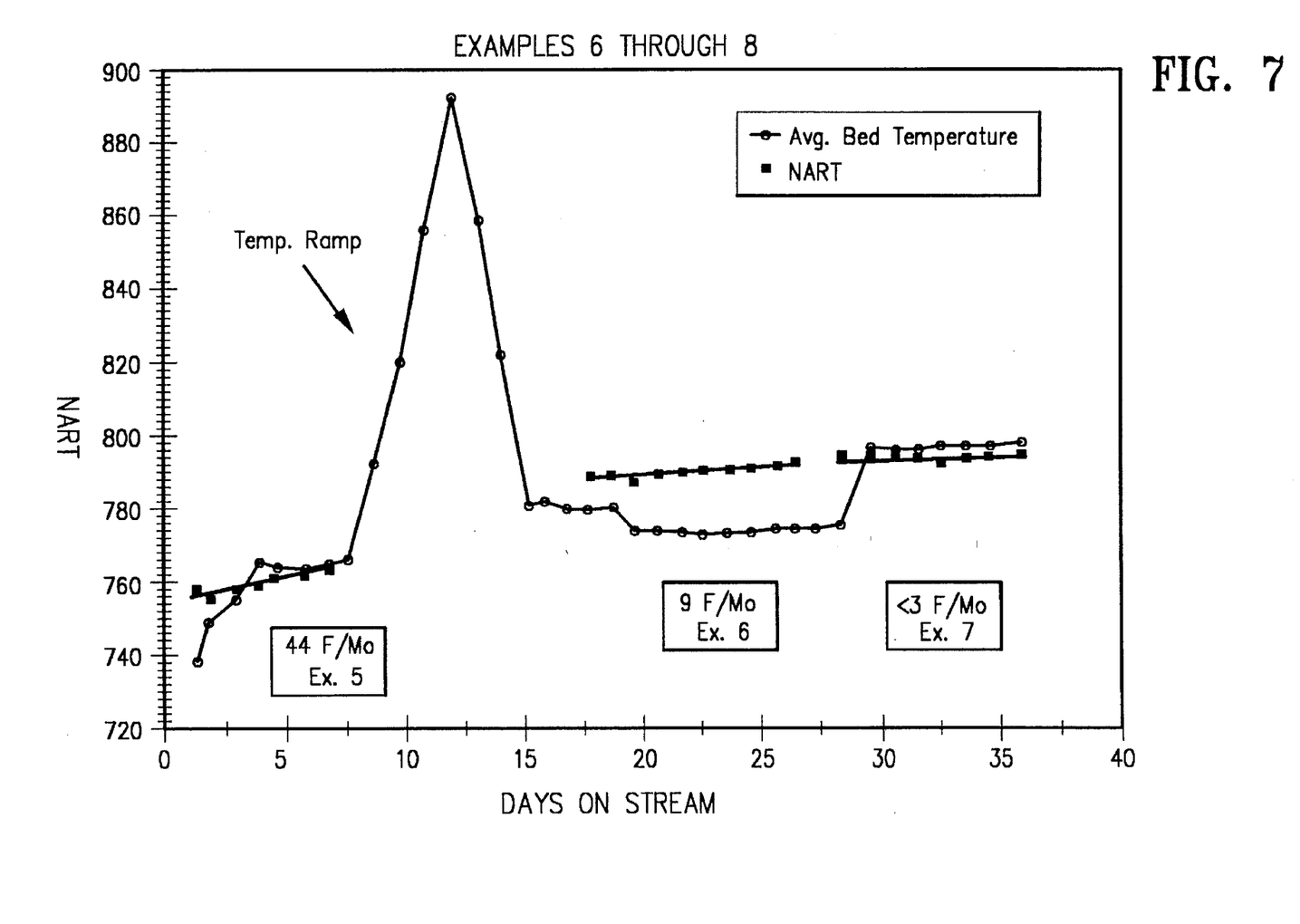

The aging rate is the number of ° F. that must be added to the reactor inlet temperature to maintain 30% toluene conversion. This is the slope of the NART plot expressed as ° F./month. The smaller the temperature adjustments, the longer the catalyst will take to reach the End of Cycle temperature and the longer the catalyst life. The conditions for the reactions are described in each Example and the NART plots are shown in FIGS. 5–7.

EXAMPLES 2 AND 3

Twenty-seven grams of extruded catalyst was loaded into a pilot unit. The temperature was set at 780° F., pressure 270 psig, and feed introduced. The process conditions are given in Table 2 below.

After establishing an initial aging/lineout rate, the inlet temperature was adjusted and then held for approximately 24 hours before the next adjustment was made. The average bed temperature and NART are shown in FIG. 5.

TABLE 2

| EXAMPLE | 2 | 3 |
|---|---|---|
| Days on Stream | 1–20 | 58–62 |
| Description | Base Case | Stabilized Catalyst |
| Feed | Toluene | Toluene |
| Catalyst, g | 27 | 27 |
| Pressure, psig | 270 | 270 |
| WHSV Toluene | 3 | 3 |
| H$_2$/Hydrocarbon | 0.7 | 0.7 |
| Aging Rate, °F./Month | 33.2 | <3 |

EXAMPLES 4 AND 5

Forty grams of extruded catalyst was mixed with a sufficient amount of crushed sand to provide a total catalyst bed of 50 cc. The temperature was set at 730° F., pressure 270 psig, and feed introduced. The process conditions are given in Table 3 below.

After establishing an initial aging/lineout rate, the inlet temperature was adjusted and then held for approximately 24 hours before the next adjustment was made. The average bed temperature and NART are shown in FIG. 6.

TABLE 3

| EXAMPLE | 4 | 5 |
|---|---|---|
| Days on Stream | 10–45 | 53–64 |
| Description | Base Case | Stabilized Catalyst |
| Feed | Non-Extracted Toluene, Blend 1 | Non-Extracted Toluene, Blend 1 |
| Catalyst, g | 40 | 40 |
| Pressure, psig | 270 | 270 |
| WHSV Toluene | 3 | 3 |
| H$_2$/Hydrocarbon | 1.0 | 1.0 |
| Aging Rate, °F./Month | 17 | <3 |

EXAMPLES 6–8

Forty grams of selectivated extruded catalyst was mixed with a sufficient amount of crushed sand to provide a total catalyst bed of 50 cc. The temperature was set at 730° F., pressure 270 psig, and feed introduced. The process conditions are given in Table 4 below.

After establishing an initial aging/lineout rate, the inlet temperature was adjusted and then held for approximately 24 hours before the next adjustment was made. The average bed temperature and NART are shown in FIG. 7.

TABLE 4

| EXAMPLE | 6 | 7 | 8 |
|---|---|---|---|
| Days on Stream | 1–7 | 18–27 | 29– |
| Description | Base Case | Stabilized Catalyst | Stabilized Catalyst |
| Feed | Pure Toluene | Non-Extracted Toluene Blend 2 | Non-Extracted Toluene Blend 1 (Ex. 4 & 5) |
| Catalyst, g | 40 | 40 | 40 |
| Pressure, psig | 270 | 270 | 270 |
| WHSV Feed | 3 | 3 | 3 |
| H$_2$/Hydrocarbon | 1.0 | 1.0 | 1.0 |
| Aging Rate, °F./Month | 44 | 9 | <3 |

EXAMPLE 9

Figure 8:
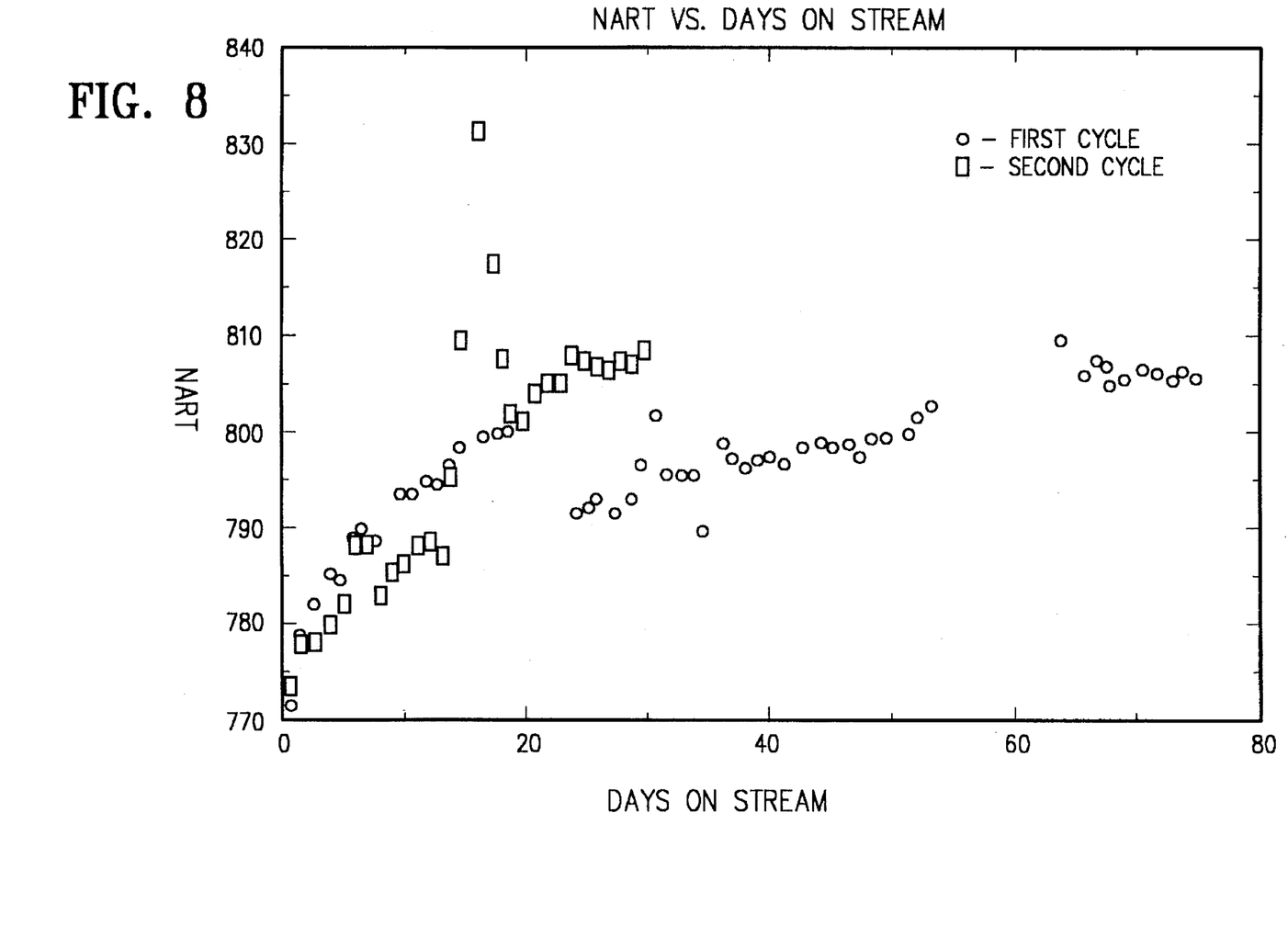
FIG. 8 is a graph showing the normalized average reactor temperature (NART) for two cycles of a toluene disproportionation reaction versus the days on stream for each cycle of the reaction.

FIG. 8 shows the first and second cycle activity for a catalyst using toluene as feedstock. The catalyst activity is determined by calculating NART, the Normalized Average Reactor Temperature. The average reactor temperature is normalized by carrying out an experiment which determines the relationship between the conversion of toluene and temperature. For the catalysts discussed here, this number is 5° F. per 1% toluene conversion.

During the first cycle, the catalyst exhibited significant aging as shown in FIG. 8. During the second cycle, the catalyst again showed significant aging, paralleling that seen in the second cycle. The catalyst was then subjected to a temperature scan of 809° F., 836° F., 867° F., 835° F., and 808° F. These temperatures are the averages of the temperatures throughout the catalyst bed. Then the temperature was adjusted to provide about 30% toluene conversion. The NART was higher than the first cycle due to additional coke lay down caused by the high temperature operation. However, as can be seen in FIG. 8, the catalyst stabilized and showed little or no aging.

What is claimed is:

1. A continuous process for disproportionating toluene, said process comprising contacting toluene with a catalyst under conditions sufficient to disproportionate toluene, said catalyst comprising ZSM-5, said catalyst being selectivated with a siliceous material, wherein said process comprises an adjustment phase and at least one steady-state phase, wherein said adjustment phase comprises introducing toluene into a reactor comprising said catalyst under conditions sufficient to increase the para-selectivity of said catalyst, wherein said steady-state phase comprises introducing toluene into said reactor under conditions sufficient to achieve essentially constant levels of toluene conversion and para-xylene selectivity, the inlet temperature of said reactor being incrementally adjusted upwardly to compensate for aging of said catalyst, wherein, during said adjustment phase, the inlet temperature of said reactor is maintained continuously for a period of at least 9 hours at a temperature which is at least 20° C. greater than the average inlet temperature during the first 10 days of operation of said steady-state phase.

2. A process according to claim 1, wherein, during said adjustment stage, the inlet temperature of said reactor is maintained continuously for a period of at least 24 hours at a temperature which is at least 20° C. greater than the average inlet temperature during the first 10 days of operation of said steady-state phase.

3. A process according to claim 1 comprising the following sequence of steps:

(a) operating said reactor under the conditions of said adjustment phase, followed by (b) operating said reactor under the conditions of a first steady-state phase, followed by (c) interrupting said first steady-state phase by increasing the inlet temperature of said reactor by at least 20° C. for a continuous period of at least 24 hours, followed by (d) operating said reactor under the conditions of a second steady-state phase, wherein the initial inlet temperature of said reactor is at least 20° C. less than the maximum inlet temperature of the reactor in step (c), wherein the aging rate of said catalyst during step (d) is less than the aging rate of said catalyst during step (b).

4. A process according to claim 1, wherein said ZSM-5 has a silica to alumina molar ratio of 60 or less.

5. A process according to claim 1, wherein said catalyst comprises at least 1 wt % of said siliceous material selectivating agent.

6. A process according to claim 1, wherein said catalyst further comprises a binder material.

7. A process according to claim 6, wherein said binder material is silica.

8. A process according to claim 4, wherein said siliceous material is deposited on said catalyst by the steps of (x) combining the bound form of ZSM-5 with an organosilicon compound; and (y) calcining the organosilicon containing material in an oxygen containing atmosphere under conditions sufficient to remove organic material therefrom and leave said siliceous material on the bound ZSM-5.

9. A process according to claim 8, wherein steps (x) and (y) are repeated at least once.

10. A process according to claim 1, wherein prior to a steady state phase, the inlet temperature of said reactor is maintained continuously for a period of at least 18 hours at a temperature which is at least 20° C. greater than the average inlet temperature during the first 100 days of operation of said steady-state phase.

11. A process according to claim 1, wherein said toluene which is introduced into said reactor is included in a liquid feedstock comprising up to about 15 wt. % of non-aromatic hydrocarbons.

* * * * *